US012597493B2

(12) United States Patent
McDonald et al.

(10) Patent No.: US 12,597,493 B2
(45) Date of Patent: Apr. 7, 2026

(54) WORKFLOWS FOR PREPARING AND ANALYZING CLINICAL SAMPLES

(71) Applicant: Waters Technologies Corporation, Milford, MA (US)

(72) Inventors: Thomas S. McDonald, Holden, MA (US); Kevin Wyndham, Upton, MA (US); Johannes Vissers, Breda (NL); Edouard S. P. Bouvier, Stow, MA (US)

(73) Assignee: Waters Technologies Corporation, Milford, MA (US)

( * ) Notice: Subject to any disclaimer, the term of this patent is extended or adjusted under 35 U.S.C. 154(b) by 1212 days.

(21) Appl. No.: 17/500,489

(22) Filed: Oct. 13, 2021

(65) Prior Publication Data

US 2022/0122699 A1 Apr. 21, 2022

Related U.S. Application Data

(60) Provisional application No. 63/150,680, filed on Feb. 18, 2021, provisional application No. 63/092,813, filed on Oct. 16, 2020.

(51) Int. Cl.
*G16H 10/40* (2018.01)
*G01N 33/68* (2006.01)
*G16H 50/80* (2018.01)

(52) U.S. Cl.
CPC ......... *G16H 10/40* (2018.01); *G01N 33/6848* (2013.01); *G16H 50/80* (2018.01)

(58) Field of Classification Search
CPC .. G01N 33/569; G01N 33/68; G01N 33/6848; G16H 10/40; G16H 50/80
See application file for complete search history.

(56) References Cited

U.S. PATENT DOCUMENTS

2017/0045526 A1* 2/2017 Thompson ......... G01N 33/6848
2021/0302416 A1* 9/2021 Soldo ............... G01N 33/54326
2021/0341492 A1* 11/2021 Hahn ................ C07K 16/2809

OTHER PUBLICATIONS

Cardozo et al. "Fast and low-cost detection of SARS-CoV-2-peptides by tandem mass spectrometry in clinical samples." Research Square. (2020).
Cardozo et al. "Fast detection of SARS-CoV-2 peptides by tandem mass spectrometry in clinical samples: proof-of-concept." Research Square. (2020).
Gouveia et al. "Proteotyping SARS-CoV-2 Virus from Nasopharyngeal Swabs: A Proof-of-Concept Focused on a 3 Min Mass Spectrometry Window." J. Proteome Res. 19(2020): 4407-4416.

(Continued)

*Primary Examiner* — Jennifer Wecker
(74) *Attorney, Agent, or Firm* — WOMBLE BOND DICKINSON (US) LLP; Deborah M. Vernon; Scott R. Breining

(57) ABSTRACT

The present disclosure relates to methods and workflows for processing and analyzing clinical samples (e.g., nasal swabs, throat swabs, plasma samples, urine, etc.) In general, the methods and workflows involve the detection of an infectious state and are improved over contemporary methods due to increased throughput with improved resolution of positive results.

12 Claims, 9 Drawing Sheets

(56)         References Cited

OTHER PUBLICATIONS

Nikolaev et al. "Mass-Spectrometric Detection of SARS-CoV-2 Virus in Scrapings of the Epithelium of the Nasopharynx of Infected Patients via Nucleocapsid N Protein." J. Proteome Res. 19(2020): 4393-4397.
Renuse et al.. "Development of mass spectrometry-based targeted assy for direct detection of novel SARS-CoV-2 coronavirus from clinical specimens." (2020).
Siefried et al. "Corona 'pool testing' increases worldwide capacities many times over." (2020).
International Search Report and Written Opinion issued in International Application No. PCT/US2021/059426 dated Jan. 20, 2022.

* cited by examiner

100

105 Samples are collected from each individual patient

110 Samples are pooled together at an n:1 ratio

115 Pooled samples are enzymatically digested

120 Pooled & digested samples are concentrated or cleaned via antibody enrichment 125 Samples are analyzed by analytical instrumentation 105 Samples are collected from each individual patient 110 Samples are pooled together at an n:1 ratio 115 Pooled samples are enzymatically digested 120 Pooled & digested samples are cleaned or concentrated via antibody enrichment 125 Samples are analyzed by analytical instrumentation 130 Samples can be cleaned up via SPE or solvent/salt mediated protein precipitation

130′   130″   130‴

205 — Samples are collected from each individual patient

210 — Individual samples are enzymatically digested

215 — Samples are pooled together at an n:1 ratio

220 — Digested and pooled samples are cleaned/concentrated via antibody enrichment 225 — Samples are analyzed by analytical instrumentation

200

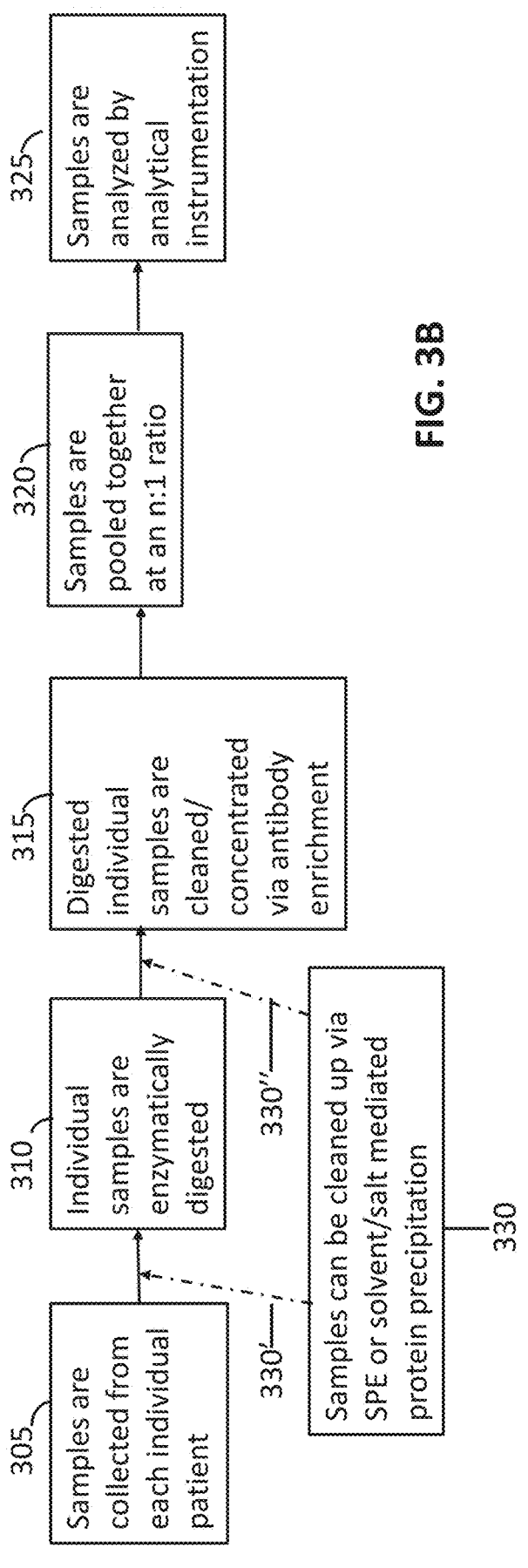

305
Samples are collected from each individual patient

310
Individual samples are enzymatically digested

315
Digested individual samples are cleaned/concentrated via antibody enrichment 320
Samples are pooled together at an n:1 ratio 325
Samples are analyzed by analytical instrumentation 330
330'
330"
Samples can be cleaned up via SPE or solvent/salt mediated protein precipitation

FIG. 3B

WORKFLOWS FOR PREPARING AND ANALYZING CLINICAL SAMPLES

CROSS-REFERENCE TO RELATED APPLICATIONS

This application claims priority and benefit to U.S. Provisional Patent Application No. 63/092,813, filed on Oct. 16, 2020, and entitled "Workflows for Preparing and Analyzing Clinical Samples." This application also claims priority and benefit to U.S. Provisional Patent Application No. 63/150, 680, filed on Feb. 18, 2021, and entitled "Workflows for Preparing and Analyzing Clinical Samples." The content of both applications are incorporated herein by reference in their entirety.

FIELD OF THE TECHNOLOGY

The present disclosure relates to methods, techniques and kits for improving analysis of clinical samples (e.g., bodily fluids, such as saliva, nasal secretions, plasma, exhaled air). More specifically, this technology relates to methods, techniques, and kits for preparing large number of samples from many different individuals for clinical analysis.

BACKGROUND

Influenza outbreaks result in about three to five million cases of severe illness and about 290,000 to 650,000 deaths per year. Other respiratory viruses such as respiratory syncytial virus (RSV) and parainfluenza take additional lives. At the end of 2019, the emergence and rapid progression of a new infection, SARS-COV-2, also known as COVID-19, escalated to pandemic status taking over 4.5 million lives worldwide in 18 months. Some infections lead to acute respiratory syndrome (ARS), acute respiratory distress syndrome (ARDS), or to severe acute respiratory syndrome (SARS) which are potentially lethal disease progressions requiring medical treatment.

Infection outbreaks and pandemics place severe strain on international health care services, especially when infected and infectious patients are asymptotic or do not yet know that they are contagious. Identifying infection prior to additional spread is needed to control outbreaks and limit the amount of critical care required to save lives. Current testing protocols test individual samples creating a bottleneck in processing samples and identifying possible contagious individuals.

SUMMARY

In general, the present technology is directed to improving throughput of clinical samples (e.g., infectious disease, such as COVID-19 testing, or other conditions, such as influenza). The present technology, in some instances, can be used to improve throughput on the sample preparation side and/or the analysis side. The present technology includes pooling (i.e., combining more than one sample (e.g., n≥2) prior to analysis). In addition, the present technology includes one or more of: enzymatic digestion, antibody enrichment, and analytical analysis, such as LC-MS.

An aspect of the present technology is directed to a method for preparing biological samples collected from mammalian subjects for clinical diagnosis via mass spectrometry. The method comprises digesting the biological samples; pooling two or more biological samples; enriching the pooled two or more biological samples using antibody immobilization; and analyzing an eluent collected from the antibody immobilization with mass spectrometry for clinical diagnosis.

Embodiments of the above aspect can include one or more of the following features. In some embodiments of the method for preparing biological samples, digestion (i.e., digesting) occurs prior to the pooling step (i.e., pooling two or more biological samples). In other embodiments, pooling occurs prior to digesting. In some embodiments, digesting the biological samples comprises mixing the biological samples with a proteolytic enzyme. In certain embodiments, the proteolytic enzyme is selected from the group consisting of trypsin, chymotrypsin, IDeS, Proteinase K, PNGaseF, and combination thereof. In some embodiments, digesting biological samples also includes a pretreatment step, which is prior to mixing the biological samples with an enzyme. The pretreatment step can aid in or prepare the biological sample for digestion. In some embodiments, the pretreatment step includes one or more of denaturation, reduction, alkylation, and combinations thereof. In some embodiments, the method includes pooling two to fifty biological samples. In some embodiments, the method includes pooling up to 1000 different biological samples (e.g., nasal swabs taken from 900 different individuals). Some embodiments use liquid chromatography-mass spectrometry for clinical diagnosis. Certain embodiments further include adding a stable labeled peptide or other subunit prior to enriching the pooled two or more biological samples. In some embodiments the clinical diagnosis is for the presence of an infectious disease, such as SARS-COV-2. Certain embodiments, also feature a solid phase extraction or solvent/salt mediated protein precipitation to clean-up samples. This clean-up step is typically applied prior to enriching the pooled two or more biological samples.

Another aspect of the present technology is directed to a method for preparing biological samples collected from mammalian subjects for clinical diagnosis via mass spectrometry. The method comprises digesting each of the biological samples individually; enriching each of the digested biological samples using antibody immobilization to create concentrated samples; pooling two or more concentrated samples to generate a pooled sample; and analyzing the pooled sampled with mass spectrometry for clinical diagnosis of an infectious disease.

Embodiments of this aspect of the technology can include one or more of the following features. In some embodiments, digesting each of the biological samples comprises mixing each of the biological samples with a proteolytic enzyme. In certain embodiments, digesting comprises a pretreatment step prior to mixing the biological samples with an enzyme. In some embodiments, pooling two or more biological samples comprises pooling up to 1000 different biological samples. In certain embodiments, mass spectrometry comprises liquid chromatography-mass spectrometry. Some embodiments of the method further include adding a stable labeled protein prior to digesting each of the biological samples individually. Certain embodiments of the method further include adding a stable labeled peptide or other subunit after creating concentrated samples and prior to analyzing the pooled sample. Some embodiments further include a solid phase extraction or solvent/salt mediated protein precipitation to clean-up samples. This clean-up step is typically applied prior to enriching the pooled two or more biological samples.

The above aspects and features provide numerous advantages. For example, the methods provided herein allow for the efficient processing of numerous clinical samples. As a result, a reduction in the amount of time needed for conducting clinical analysis can be achieved and time-sensitive information regarding the presence or rate of an infectious disease can be acted upon.

DETAILED DESCRIPTION OF THE DRAWINGS

The technology will be more fully understood from the following detailed description taken in conjunction with the accompanying drawings, in which:

FIG. 3B illustrates possible/optional time points within the method of FIG. 3A in which samples can be cleaned up.

DETAILED DESCRIPTION

Figure 1A:
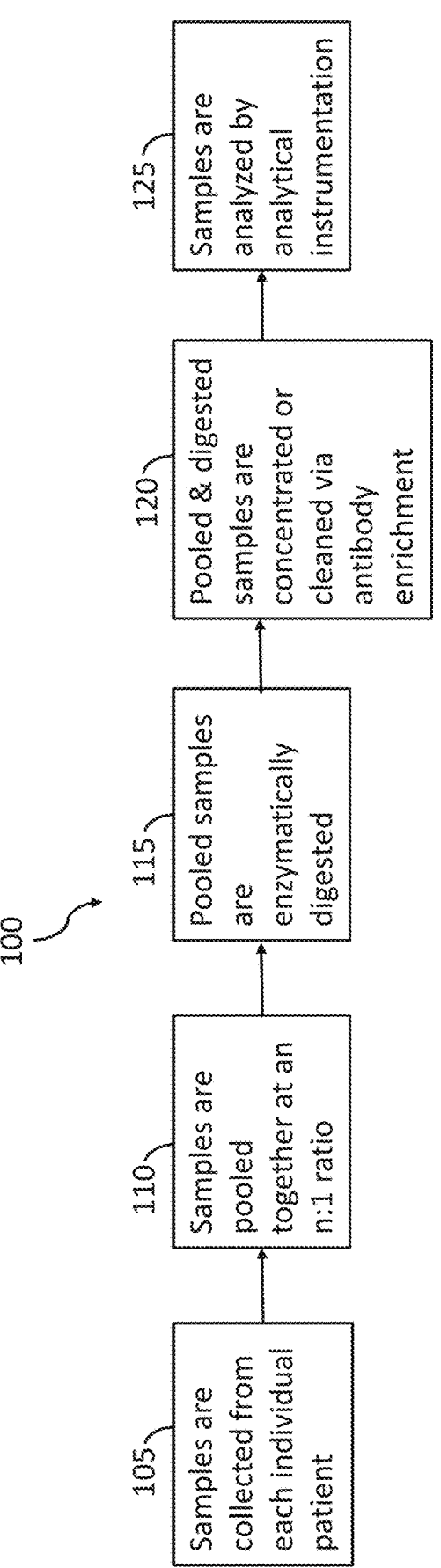
FIG. 1A illustrates a method in accordance with an embodiment of the present technology in which individual samples taken from mammalian subjects are pooled together prior to further processing.

When an infectious outbreak occurs, critical information can be obtained by testing large portions of the population frequently. For example, by testing a large segment of the population residing in a town, working within a building or campus, or using a public space such as a school, a governmental building, or public transportation center, information on the spread of the infection can be gathered in real-time and used to decrease infection rates and hopefully control the disease through quarantine and other risk mitigating behaviors. Gathering and processing the data required to make time-sensitive decisions on risk mitigation requires new protocols and testing efficiencies to be developed. Current processing of a sample using PCR techniques takes too long to process samples and collect data especially from a large segment of a possibly infected population.

In general, the present technology is directed to methods and workflows for preparing and analyzing clinical samples, such as biological samples taken from mammalian subjects (e.g., nasal swabs, collected saliva, dried blood spots, urine or excrement, breathalyzer filter strip or other collected exhaled air sample). The workflows and methods of the present technology include pooling a number of samples together at some point during the workflow to gain efficiencies in the amount of time to process numerous samples. In addition, many of the embodiments of the present technology include steps, such as digestion and antibody enrichment to obtain better resolution and detection using mass spectrometry.

Pooling is used to increase the throughput of samples in a shorter amount of time. Pooled testing is used as a screening approach, in which a number of samples from different individuals are combined to form a pooled sample. The pooled sample is tested first. If negative, all members of the pool can be given a negative result immediately, saving the cost and time of testing each sample individually. If the pool tests positive, re-testing of some subunit of the pool (i.e., single samples from individuals, or some smaller pool of combined samples) is tested to identify the number of positives within the pool.

Enzymatic digestion can be utilized to break down peptides to obtain better resolution in the results. Enzymes for use for digestion in the present technology include, but are not limited to, proteolytic enzymes (e.g., trypsin, chymotrypsin, IDeS, Proteinase K, PNGaseF, etc.). By breaking down samples into smaller subunits such as proteins, collected samples can be analyzed for the presence of a target protein, which is indicative of infection (e.g., the spike protein from a corona virus). Enzymatic digestion may be combined with a variety of pretreatment steps (e.g., denaturation, reduction, and/or alkylation). These pretreatment steps can be used to prepare the sample for digestion.

Antibody enrichment can be used to help magnify the results for detection purposes (e.g. MS detection). In general, antibody enrichment can be accomplished by mixing digested samples with antibody-immobilized beads or into antibody immobilized plates, columns, tips or other format followed by washing and elution. The selected antibodies preferentially bind with the target protein. As a result, target proteins from the digested sample can be trapped/retained by the antibody-immobilized beads, plates, or other format while other proteins are washed away. Antibody enrichment enriches the processed sample to contain a higher concentration of the targeted species-thereby making detection of the targeted species easier or within detection limits in instruments.

The present technology provides various methods and workflow for improved analysis of clinical samples. In particular, the present technology provides a number of embodiments, in which the order of pooling, digesting, and enriching a sample collected from a mammalian subject are provided in order to enhance detection and analysis, specifically using a mass spectrometer.

Pooling

In general, pooling is used to increase the throughput of samples analyzed. That is, a number (n) of samples from different sources (e.g., different mammalian patients who are testing for the presences of an infectious disease, such as, for example, SARS-COV-2) are combined together and analyzed together. The exact number of samples combined together is typically dependent on positivity rates and any other factors(s) that might complicate the results from a pooled assay. In certain embodiments, the n is selected based upon plate or other consumable format (e.g., 96 well plate, etc.).

In certain embodiments, the value of n ranges from 2 to 50. In others, the n value ranges from 250 or 500. In some instances, the n can range from 2 to a few thousand. Pooling workflows can include creating pools from the entirety of (n) different samples. In other workflows, an algorithmic/statistical approach, such as each sample is mixed into multiple pools to alleviate some retesting opportunities, is utilized. In some embodiments, a matrix approach is used to make a grid of combined patients forming a plurality of smaller pools that are used to cover subsets of the (n) different samples. In certain embodiments, samples are divided into two or more samples such that a reference sample that is not mixed in a pool can be maintained for confirmatory purposes.

Digestion

Enzymatic digestion is the process of breaking down a sample into subunits, such as proteins. Prior to analysis, enzymes, such as, trypsin, are added to break down the sample. In addition to breaking down the sample, digestion can be combined with a variety of pretreatment steps, such as denaturation, reduction, and/or alkylation, to prepare the sample for a more efficient/resilient digestion. In addition to pretreatment steps, sample clean-up steps (i.e., processing to clean-up or remove interfering portions of the sample can be conducted before, during, or after digestion. For example, solid phase extraction (SPE) or solvent/salt mediated protein precipitation can be applied to remove portions of the sample that are unwanted or could interfere with clinical sample analysis.

Antibody Enrichment

Various embodiments of the technology described herein make use of an affinity ligand that specifically binds to a viral antigen. For example, in some embodiments, the affinity ligand can be an antibody-based affinity ligand, which specifically recognizes and binds to an antigen via the three complementarity determining regions (CDRs) characteristic of an antibody heavy chain variable region (VH), and the three CDRs characteristic of an antibody light chain variable region (VL). Antibody-based affinity ligands can include, for example, monoclonal antibodies (and antigen-binding portions thereof), polyclonal antibodies (and antigen-binding portions thereof), and antigen-binding fragments of antibodies, including but not limited to Fab', F(ab')2, Fab, Fv, and half-antibody fragments. In some embodiments, the affinity ligand is an intact, full-length antibody. In some embodiments, the antibody is a recombinant monoclonal antibody. The antibody can be of any isotype, including IgG (e.g., IgG1, IgG2, IgG3, or IgG4), IgM, IgA, or IgE. In some embodiments the antibody is a polyclonal antibody. A polyclonal antibody preparation generally comprises a plurality of antibody molecules that collectively recognize a plurality of epitopes on a target of interest. For example, a polyclonal antibody raised against a viral particle (e.g., SARS-COV-2) contains a plurality of antibody molecules that can collectively recognize multiple viral (e.g., SARS-COV-2) antigens. In some embodiments, the polyclonal antibody can be a mouse polyclonal antibody, a rabbit polyclonal antibody, a goat polyclonal antibody, or a rat polyclonal antibody. Other antibody-based affinity ligands include antigen-binding molecules that comprise the VH and/or VL region of an antibody, or a portion thereof, optionally joined by a linker. Exemplary ligands include an scFv, a diabody, a triabody, a nanobody, a VHH antibody, a domain antibody, a variable domain from an immunoglobulin new antigen receptor (vNAR) or a dual-variable domain immunoglobulin (DVD-Ig). In some embodiments, an antibody-based affinity ligand can be bispecific, binding two distinct antigens. In some embodiments, an antibody-based affinity ligand can be biparatopic, binding two distinct epitopes on the same antigen. In other embodiments, an antibody-based affinity ligand can be trispecific or multispecific.

Affinity ligands for use in the technology provided herein can specifically bind to a viral antigen. Specific binding refers to the ability of a ligand to recognize and bind to a specific protein structure (epitope), rather than to proteins generally. By way of example, a ligand that specifically binds to an antigen can capture that antigen from a protein mixture, without binding to other proteins present in the mixture. In some embodiments, an affinity ligand specifically binds to a viral antigen with a dissociation constant ($K_D$) of $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, or less. In some embodiments, an affinity ligand specifically binds to a viral antigen with a dissociation constant ($K_D$) of $10^{-7}$ M or less. In some embodiments, an affinity ligand specifically binds to a viral antigen with a dissociation constant ($K_D$) of $10^{-9}$ M or less. In some embodiments, an affinity ligand specifically binds to a viral antigen with a dissociation constant ($K_D$) of $10^{-7}$ M to $10^{-12}$ M. In some embodiments, the dissociation constant of an affinity ligand can be measured using surface plasmon resonance. In other embodiments, the dissociation constant of an affinity ligand can be measured using Bio-Layer Interferometery (BLI).

The workflows described herein can be used to detect viral particles of any type, using an affinity ligand that specifically binds to a viral antigen present on the viral particle to be detected.

In some embodiments, the affinity ligand can specifically bind to a coronavirus antigen. For example, in some embodiments, the affinity ligand can specifically bind a SARS-CoV-2 antigen. In some embodiments, the affinity ligand can specifically bind to the SARS-CoV-2 spike protein. In some embodiments, the affinity ligand can specifically bind to the S1 subunit of the SARS-COV-2 spike protein. In some embodiments, the affinity ligand can be an antibody-based affinity ligand that specifically binds to receptor binding domain of the SARS-CoV-2 spike protein. For example, in some embodiments, the affinity ligand can be a monoclonal antibody, polyclonal antibody, antibody fragment, scFv or vNAR (variable domain from an immunoglobulin new antigen receptor) that specifically binds to the S1 subunit of the SARS-COV-2 spike protein.

In other embodiments, the affinity ligand can specifically bind to an influenza antigen. For example, in some embodiments, the affinity ligand can specifically bind to an influenza hemagglutinin (HA) protein. In some embodiments, the affinity ligand can be an antibody-based affinity ligand that specifically binds to the influenza HA protein. For example, in some embodiments, the affinity ligand can be a monoclonal antibody, polyclonal antibody, antibody fragment, or scFv that specifically binds to the influenza HA protein. In other embodiments, the affinity ligand can specifically bind to an influenza neuraminidase protein. In some embodiments, the affinity ligand can be an antibody-based affinity ligand that specifically binds to the influenza neuraminidase protein. For example, in some embodiments, the affinity ligand can be a monoclonal antibody, polyclonal antibody, antibody fragment, or scFv that specifically binds to the influenza neuraminidase protein.

The affinity ligands used in the workflows described herein can, in some embodiments, be immobilized on a substrate or resin. Suitable substrates include, but are not limited to, beads, particles, plates, etc. For example, in some embodiments, the affinity ligand can be immobilized on beads, e.g., agarose beads, sepharose beads, polymethacrylate beads, silica beads, organosilica beads, dextran beads, or Sephadex® beads. In some embodiments, the beads are microbeads. For example, in some embodiments, the beads can have a diameter of 200 nm or less, e.g., 150 nm or less, 100 nm or less, 50 nm or less, or 20 nm or less. In some embodiments, the beads can have a diameter of about 50-150 nm. In some embodiments, the beads can have a charged surface, e.g., a positively charged surface, or a negatively charged surface. In some embodiments, the beads can be magnetic. Beads comprising immobilized affinity resin can be collected following the capture and/or wash steps using standard techniques, including, for example, centrifugation, sedimentation, filtration, or (in the case of magnetic beads) exposure to a magnetic field.

In some embodiments, beads comprising immobilized affinity ligand can be packed in a column, e.g., a chromatography column. In such embodiments, the capture step, the wash step, and/or the elution step can be performed by passing material through the column. For example, a sample comprising viral particles and/or viral antigens (e.g., from a proteolytic digest) can be passed through a column packed with beads comprising immobilized affinity ligand, and the flow rate can be adjusted to allow specific binding of a viral antigen to the affinity ligand. The column can be washed with a wash buffer to remove unbound material, and viral particles and/or viral antigens can subsequently be eluted from the column using an elution buffer. In some embodiments, the column can be operated under pressure (HPLC). In such embodiments, it can be desirable to use beads that are not compressible, such as silica or organosilica beads. In some embodiments, the HPLC column can be operably linked to a system for MS detection.

In other embodiments, the affinity ligand can be immobilized on a filter plate. In some embodiments, the affinity ligand can be immobilized on a multi-well plate, e.g., a 96-well plate. In such embodiments, the capture step, the wash step, and/or the elution step can be performed by addition and removal of material from the plate. For example, in the capture step, a sample can be loaded onto the plate, and incubated for a period of time sufficient for viral particles and/or viral antigens to bind the affinity ligand. Unbound material can be removed (e.g., by suctioning or pipetting), and the bound material can be washed with a wash buffer to remove unbound material. The wash buffer can be removed, and the bound material can be analyzed by MS. Alternatively, following removal of the wash buffer, viral particles and/or viral antigens can be eluted from the plate by addition of an elution buffer, and/or can be subjected to proteolytic digestion, prior to analysis by MS.

An affinity ligand can be attached to the substrate or resin using any suitable method, such as, for example, Michael addition, reductive amination, carbodiimide facilitated dehydration, nucleophilic substitution, and vapor deposition.

Antigen Capture/Antibody Enrichment

Viral particles or viral antigens can be enriched in a sample (e.g., a sample known or suspected to contain viral particles, as described herein) by contacting the sample with an affinity ligand that specifically binds to a viral antigen. The volume of the sample can be adjusted depending on the quantity of antigen needed for detection.

In some embodiments, a resin or substrate containing the affinity ligand can be pre-treated with a protein or peptide that is not specifically bound by the affinity ligand (e.g., a non-viral protein or peptide) to block non-specific binding interactions with the resin or substrate, prior to contacting the affinity ligand with the sample. For example, in some embodiments, the affinity ligand can be pre-treated with bovine serum albumin (BSA). Appropriate concentrations of BSA suitable for blocking can be readily determined. In some embodiments, the affinity ligand can be pre-treated with 100 µg/mL to 10 mg/mL BSA solution. Unbound blocking agent can be removed by washing using a suitable wash buffer, e.g., purified water or phosphate buffered saline (PBS).

In some embodiments, the resin or substrate comprising the affinity ligand can be equilibrated with an equilibration buffer prior to contact with the sample. In some embodiments, the equilibration buffer is the same buffer used to prepare the sample. The sample containing or suspected to contain viral particles can be loaded onto the resin or substrate containing the affinity ligand. The sample is maintained or incubated with the resin or substrate for a period of time sufficient for viral antigens in the sample to bind the affinity ligand. In some embodiments, the sample is incubated with the affinity ligand for up to 60 minutes. In some embodiments, the sample is incubated with the affinity ligand for up to 30 minutes. In some embodiments, the sample is incubated with the affinity ligand for up to 20 minutes. In some embodiments, the sample is incubated with the affinity ligand for up to 10 minutes. In some embodiments, the sample is incubated with the affinity ligand for up to 5 minutes. In some embodiments, the sample is incubated with the affinity ligand for about 1, about 2, about 3, about 4, about 5 about 6, about 7, about 8, about 9, or about 10 minutes. In some embodiments, the incubation can be performed with gentle mixing.

Unbound components of the sample can be removed by washing the resin or substrate with a wash buffer. Suitable wash buffers will remove unbound sample components without disrupting the binding of the affinity ligand to the target antigen. In some embodiments, the wash buffer can be purified water or PBS.

Detection of Viral Antigens Using Ambient Ionization MS

Direct ambient ionization from DESI, MALDI or REIMS can be used to detect viral antigens directly following the capture step, without elution, by focusing the ionization source to a concentrated area of analyte adsorbed to an affinity resin (e.g., beads or substrate coated with affinity ligand).

Mass spectrometers with Atmospheric Pressure Ionization ("API") ion sources utilize a sampling orifice or capillary in or near the ion source to allow the ions that are created at atmospheric pressure ("AP") to be admitted into the vacuum chamber containing the mass analyzer. As a result, sample ionization can occur at ambient or soft conditions.

Desorption electrospray ionization (DESI) is an ambient ionization technique that can be used in mass spectrometry for chemical analysis. It is an atmospheric pressure ion source that ionizes gases, liquids and solids in open air under ambient conditions. DESI is a combination of electrospray (ESI) and desorption (DI) ionization methods. Ionization can take place by directing an electrically charged mist to a sample surface. The electrospray mist can be attracted to the surface by applying a voltage on the sample or sample holder. After ionization, the ions can travel through air into the atmospheric pressure interface which can be connected to a mass spectrometer.

Matrix Assisted Laser Desorption Ionization ("MALDI") is a soft ionization technique that involves a laser striking a matrix of small molecules to make the analyte molecules into the gas phase without fragmenting or decomposing them. MALDI has been used to analyze biomolecules, such as, peptides, lipids, saccharides, and other organic macromolecules.

Rapid Evaporative Ionization Mass Spectrometry (REIMS) is an ionization technique that can be used as a source for direct analysis of samples by mass spectrometry. REIMS is an atmospheric pressure ion source that can ionize gases, liquids or solids in open air under ambient conditions. The REIMS ionization source can be a probe (e.g., electrodes) that can be used to remotely test the samples.

Elution from the Antibody Enrichment/Affinity Capture Step

In some embodiments, captured viral particles or viral antigens are eluted from the affinity ligand prior to analysis. Accordingly, viral particles or viral antigens can be eluted from an affinity ligand by contacting the ligand with an elution buffer. The affinity ligand can be incubated with the elution buffer for a period of time sufficient for the antigen to elute from the affinity ligand. For example, the affinity ligand can be incubated with the elution buffer for up to 60 minutes, up to 30 minutes, up to 20 minutes, up to 10 minutes, or up to 5 minutes. In some embodiments, the affinity ligand can be incubated with the elution buffer for about 1, about 2, about 3, about 4, about 5 about 6, about 7, about 8, about 9, or about 10 minutes. This process generates an eluent that is enriched with the target viral particle/viral antigen (e.g., target protein indicative of infection.)

In some embodiments, direct elution into a mass spectrometer is possible. In such approaches, the captured analytes can be eluted with volatile mobile phases. These can include but are not limited to varying concentrations of organic solvent, like acetonitrile, methanol, ethanol, and isopropanol, with or without a pH modifier, such as formic acid, acetic acid, difluoroacetic acid, trifluoroacetic acid, ammonia, ammonium formate, ammonium acetate, ammonium carbonate, ammonium bicarbonate or ammonium hydroxide. A volatile reducing agent can optionally be added to these as well, including but not limited to betamercaptoethanol or triethylphosphine. An apparatus for rapidly developing a single use well of affinity resin can outfitted in front of the mass spectrometry. An exemplary apparatus for this analytical approach would be a machine with capabilities similar to the RapidFire 400 instrument manufactured by Agilent Corporation (Santa Clara, CA).

In yet other embodiments, a column packed with affinity resin can be used with a liquid chromatograph to serially process pooled samples. Effluent containing the sample can be detected with an optical detector or a mass spectrometer. In this embodiment, it can be preferable for the ligand to have properties of low carryover and amenability to being rapidly cycled through load, wash and elute steps with repetition many times over. In some embodiments, the effluent of the affinity column can be directed to an online immobilized enzyme reaction, wherein proteolytic digestion can be performed ahead of analyte detection.

In general, the technology provides workflows that not only increase the throughput of results by pooling, but also allows for improved throughput on sample preparation side as one or more sample preparation steps are applied to the pooled sample instead of individual samples. The present technology provides various improved methods for preparation and analysis of clinical samples. These workflows include pooling, digestion, and antibody enrichment of the clinical samples. The workflows can also feature sample pretreatment steps to digestion, sample clean-up steps to remove interfering or unwanted materials from the sample, and/or assay precision to improve detection results using mass spectrometry.

In some embodiments, the technology includes a workflow in which pooling occurs before samples are digested and enriched. In certain embodiments, the workflow of the present technology includes pooling of samples between digestion and enrichments steps. In other embodiments, the workflow includes pooling of samples after digestion and enrichment steps, but before analytical detection. Analytical detection can include one or more of LC-Optical (UV, MALS, Fluorescence), LC-MS, LC-MS/MS, AIMS (DESI, MALDI, REIMS, ASAP). The workflows of the present technology can also include one or more sample clean up steps, such as SPE or solvent/salt mediated protein precipitation. In some embodiments, the workflows can also include the addition of a stable label protein, peptide, or other submit to improve assay precision.

Referring to FIG. 1A, shown is an illustration of a method 100 of preparing a clinical sample for analysis. In method 100, samples are collected from each individual patient to be tested for the presence of an infectious disease (step 105). The samples are pooled together at an n:1 ratio (step 110). N is the total number of individuals in a pooled sample. In some embodiments, n equals the total number of individuals to be analyzed in a particular analysis. In other embodiments, n is some subset or lesser number than the total number of individuals to be tested. In step 115, the pooled sample is enzymatically digested to form a pooled and digested sample. Next, in step 120, the pooled and digested sample is subjected to antibody enrichment, which results in the targeted proteins being captured or retained on a substrate and the removal of the remainder of the sample. After antibody enrichment, the concentrated sample which is contained on the substrate or eluted therefrom is analyzed by analytical instrumentation (125), which is typically involves mass spectrometry.

Figure 1B:
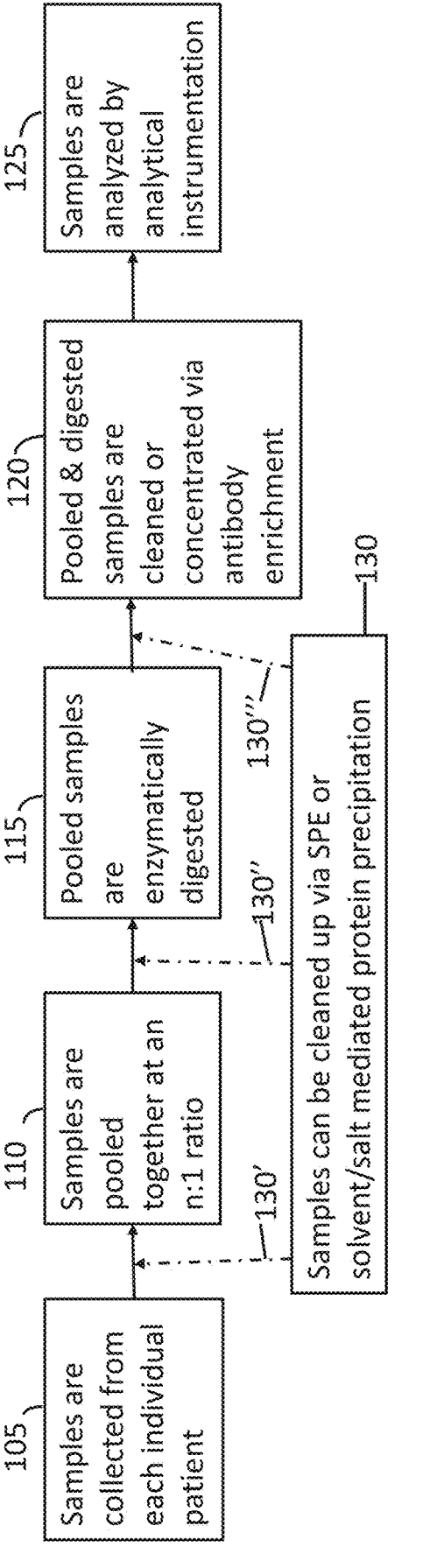
FIG. 1B illustrates possible/optional time points within the method of FIG. 1A in which samples can be cleaned up.
Figure 1C:
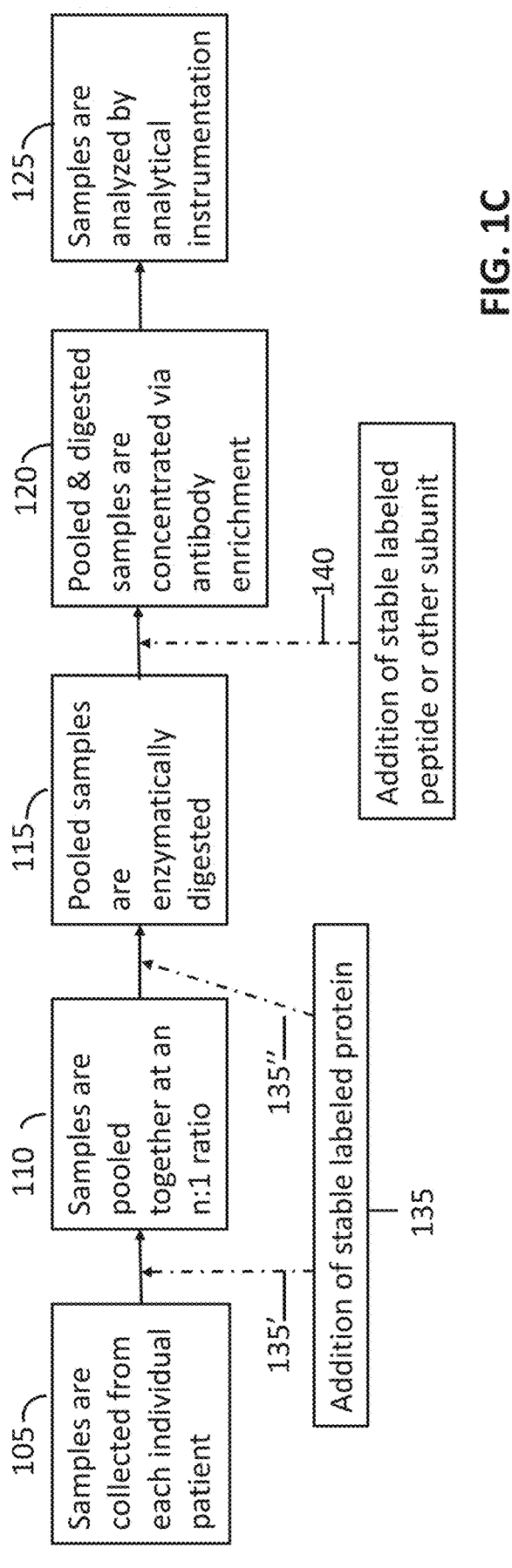
FIG. 1C illustrates possible/optional time points within the method of FIG. 1A in which assay precision additions can be introduced.

FIG. 1B and FIG. 1C illustrate possible variations to method 100 shown in FIG. 1A. The detection results from method 100 may be, in some embodiments, further improved by the incorporation of a sample clean-up step (130). The clean-up step 130 can remove unwanted material from the collected, pooled, and/or digested samples. Exemplary clean-up processing of the sample includes, but is not limited to SPE and solvent/salt mediated protein precipitation. FIG. 1B illustrates three possible locations (130', 130" and 130''') where sample clean-up can be introduced into method 100. It should be understood by those of ordinary skill in the art, that multiple clean-up steps can be applied depending on the type of collected sample. In addition, the multiple clean-up steps can occur all at one of the three possible locations (e.g., at 130") or at multiple locations (e.g., 130' and 130''').

The method 100 can also include the addition of stable labeled materials (e.g., proteins, peptides, or other subunits) to increase assay precision for MS detection. In particular, stable labeled proteins can be added (at location 135) to increase precision any time before digestion. See, for example, locations 135' and 135" as possible locations for the addition of stable labeled protein. Stable labeled peptides or other subunits can be optionally added to the workflow at location 140. Some embodiments include both the addition of stable labeled protein at location 135 and addition of stable labeled peptide at location 140. Others include just one of (i.e., either or) addition steps at location 135 and at location 140.

Figure 2A:
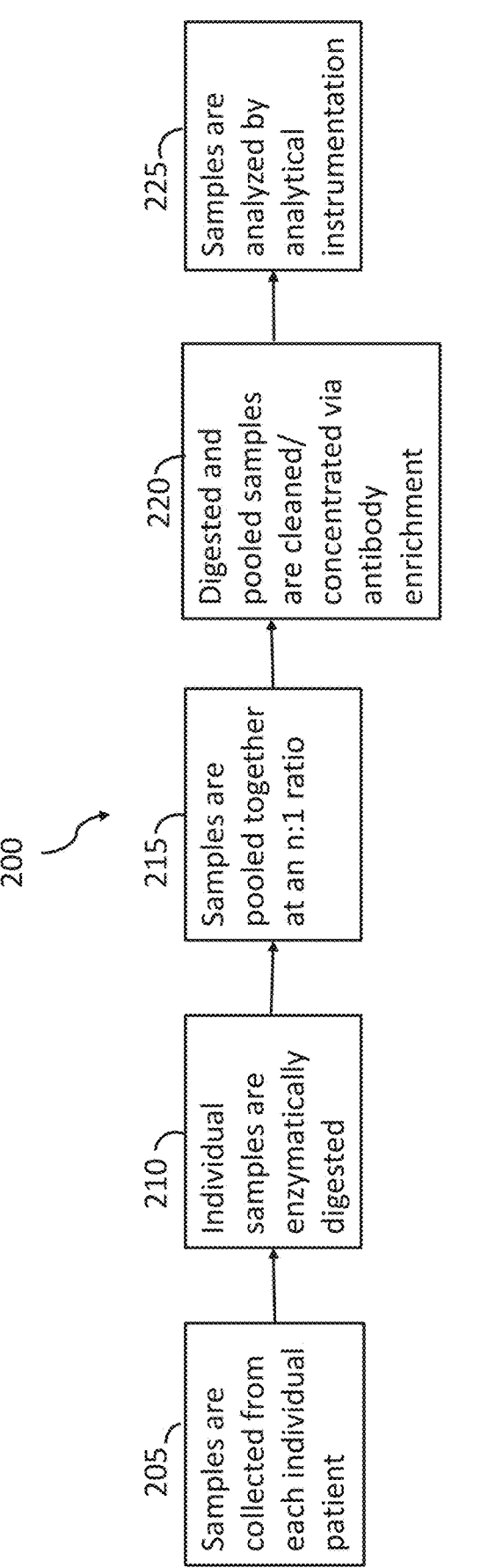
FIG. 2A illustrates a method in accordance with an embodiment of the present technology in which individual samples are digested prior to pooling.

Referring to FIG. 2A, shown is an illustration of a method 200 of preparing a clinical sample for analysis. In method 200, samples are collected from each individual patient to be tested for the presence of an infectious disease (step 205). Prior to pooling the individual samples, digestion is applied in step 210. In some embodiments, digestion to individual samples can occur in the collection vessel and thus do not add significant time or resources to the overall workflow. After the individual samples are enzymatically digested in step 210, the digested samples are pooled together at an n:1 ratio (step 215). Next, in step 220, the digested and pooled sample is subjected to antibody enrichment, which results in the targeted proteins being captured or retained on a substrate, while the remainder of the sample is removed. After antibody enrichment, the concentrated sample which is contained on the substrate or eluted therefrom is analyzed by analytical instrumentation (125), which is typically involves mass spectrometry.

Figure 2B:
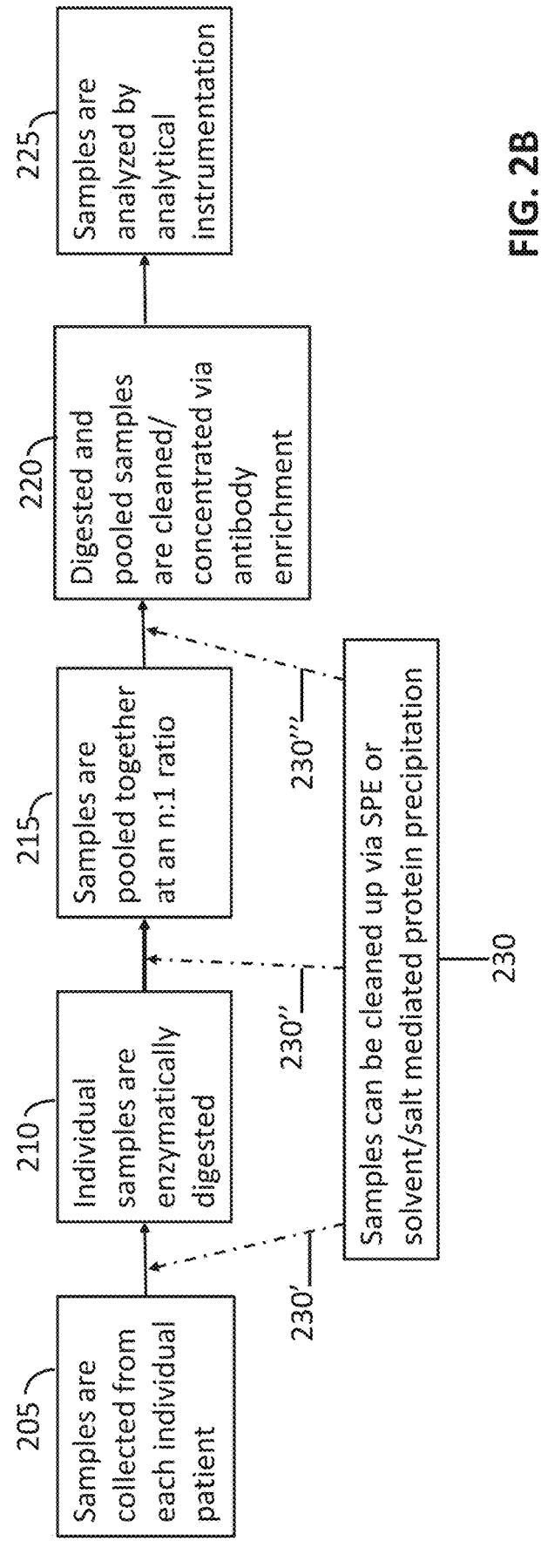
FIG. 2B illustrates possible/optional time points within the method of FIG. 2A in which samples can be cleaned up.
Figure 2C:
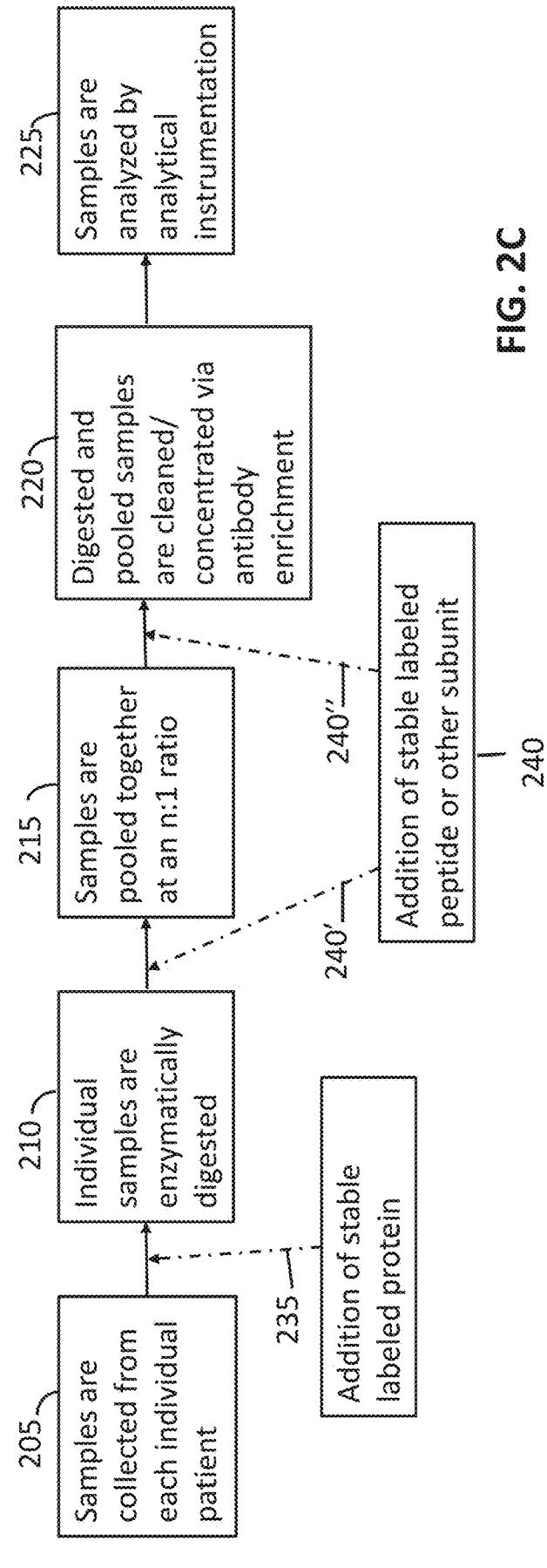
FIG. 2C illustrates possible/optional time points within the method of FIG. 2A in which assay precision additions can be introduced.

FIG. 2B and FIG. 2C illustrate possible variations to method 200 shown in FIG. 2A. The detection results from method 200 may be, in some embodiments, further improved by the incorporation of a sample clean-up step (230). The clean-up step 230 can remove unwanted material from the collected, digested, and/or pooled samples. Exemplary clean-up processing of the sample includes, but is not limited to SPE and solvent/salt mediated protein precipitation. FIG. 2B illustrates three possible locations (230', 230" and 230'") where sample clean-up can be introduced into method 200. It should be understood by those of ordinary skill in the art, that multiple clean-up steps can be applied depending on the type of collected sample. In addition, the multiple clean-up steps can occur all at one of the three possible locations (e.g., at 230') or at multiple locations (e.g., 230' and 230").

Method 200 can also include the addition of stable labeled materials (e.g., proteins, peptides, or other subunits) to increase assay precision for MS detection. In particular, stable labeled proteins can be added (235) to increase precision before digestion. Stable labeled peptides or other subunits (240) can also be optionally added to the workflow. See, for example, locations 240' and 240" as possible locations for the addition of stable labeled peptides or other protein subunit. Some embodiments include both the addition of stable labeled protein 235 and addition of stable labeled peptide 240. Others include just one of (i.e., either or) addition steps 235 and 240.

Figure 3A:
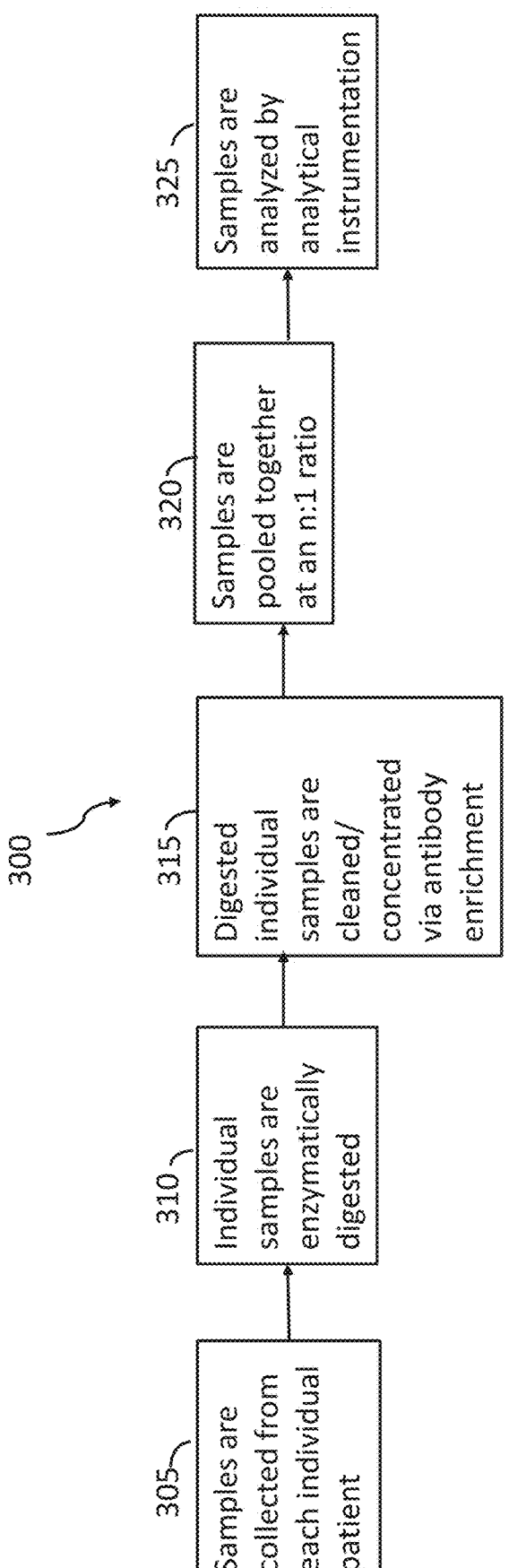
FIG. 3A illustrates a method in accordance with an embodiment of the present technology in which individual samples are digested and concentrated prior to pooling.
Figure 3C:
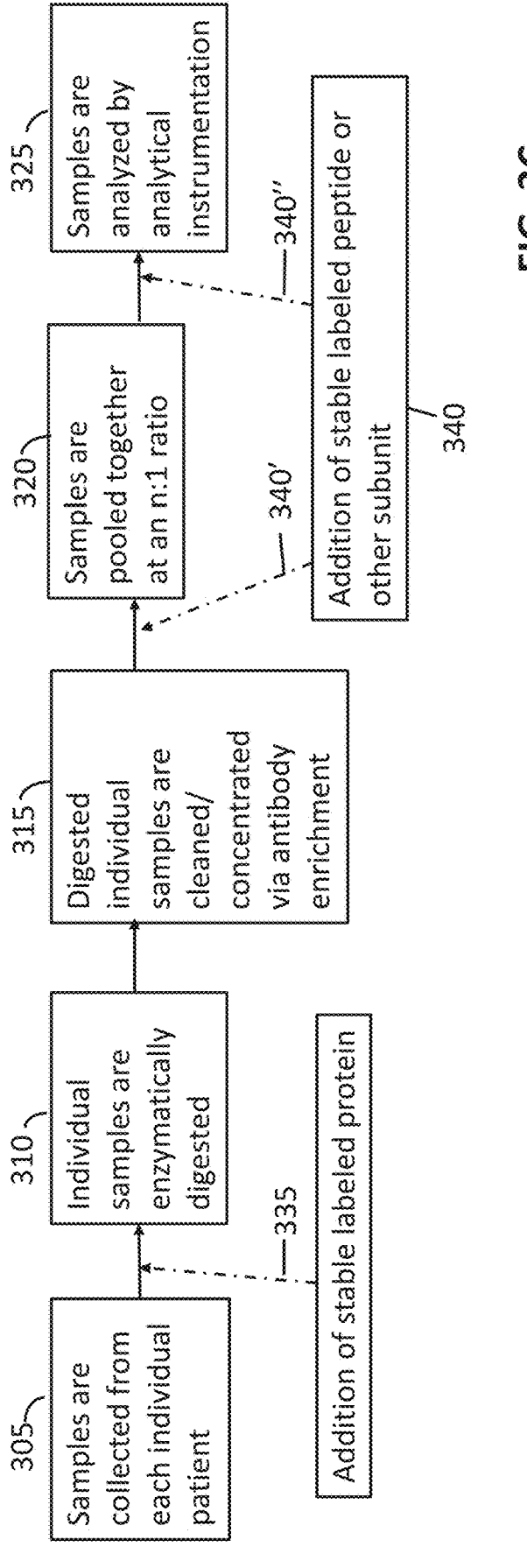
FIG. 3C illustrates possible/optional time points within the method of FIG. 3A in which assay precision additions can be introduced.

Referring to FIG. 3A, shown is an illustration of a method 200 of preparing a clinical sample for analysis. In method 300, samples are collected from each individual patient and prepared prior to pooling. In some embodiments of method 300, digestion and antibody enrichment steps occur within a collection vessel with minimal oversight. As a result, individual samples can be processed prior to pooling without a loss of efficiency. In step 305 samples are collected from individuals. Next, individual samples are enzymatically digested (step 310). In step 315, each of the digested individual samples is cleaned/concentrated via antibody enrichment. The individual samples, which have each been digested and enriched, are then pooled together to form a pooled sample in step 320. To create the pooled sample, the individual samples are eluted from the immobilized antibodies (i.e., from the affinity capture resin/substrate). The pooled sample is then analyzed in step 325, typically by mass spectrometry for the presence of the infectious disease (i.e., presence of the target protein which is indicative of infection).

Like methods 100 and 200, method 300, in some embodiments, can be improved by the addition of clean-up or assay precision steps. Referring to FIG. 3B, two possible locations (330' and 330") where sample clean-up (330) can be introduced into method 300 are shown. It should be understood by those of ordinary skill in the art, that multiple clean-up steps can be applied depending on the type of collected sample. In addition, the multiple clean-up steps can occur all at one of the three possible locations (e.g., at 330") or at both locations 330' and 330".

Method 300 can also include the addition of stable labeled materials (e.g., proteins, peptides, or other subunits) to increase assay precision for MS detection. In particular, stable labeled proteins can be added (335) to increase precision before digestion. Stable labeled peptides or other subunits (340) can also be optionally added to the workflow. See, for example, locations 340' and 340" as possible locations for the addition of stable labeled peptides or other protein subunit. Some embodiments include both the addition of stable labeled protein 335 and addition of stable labeled peptide 340. Others include just one of (i.e., either or) addition steps 335 and 340.

While the above methods 100, 200, and 300 illustrate workflow in which samples are collected from individual patients or subjects, the collection from individual subjects need not be discrete. For example, the collection from a number of different individuals can come from a single collection source, such as a filter or a specimen from a public utility (e.g., sewer system) or public confined space (e.g., air filter in a transportation center or campus classroom). A workflow using a single collection source can be used to determine the risk of infection or positivity rate at a location.

If individual samples are collected, these samples can be used for not only the determination of a positivity rate of the pool, but also for the diagnosis of individual mammalian patients from the pool. Typically, individually collected samples will be divided, and a portion retained from combination within a pool for confirmatory purposes.

Samples used in the present technology can be collected in a number of different formats/matrices; including: nasal swabs, mouth/throat swabs, saliva specimens in collection vessel, plasma, dried bloods spots, urine, excrement, filter from a breathalyzer/analyzer for exhaled air. In some embodiments, the sample is extracted from the collection device. For example, sample is extracted from a swab or filter paper. In other embodiments, the sample is collected in a container. Preprocessing or pretreatment steps, such as filtering, centrifuging, denaturing, reducing, etc. can be applied to the sample prior to the required steps of pooling, digesting, and enriching (no matter what order the required steps are in e.g., method 100, 200, or 300).

While this disclosure has been particularly shown and described with reference to example embodiments thereof, it will be understood by those skilled in the art that various changes in form and details may be made therein without departing from the scope of the technology encompassed by the appended claims. For example, while mass spectrometry detection has been described as the analytical instrumentation applied to the clinical samples, other analytical techniques may be applied or preferred, such as for example, LC-UV or fluorescence.

What is claimed is:

1. A method for preparing biological samples collected from different mammalian subjects for clinical diagnosis via mass spectrometry, the method comprising:

pooling two or more biological samples;

digesting the pooled two or more biological samples;

enriching the pooled two or more biological samples, wherein enriching comprises contacting the samples with an antibody-based affinity ligand immobilized on a substrate, followed by washing and elution to form an eluate; and analyzing the eluate with mass spectrometry for clinical diagnosis.

2. The method of claim 1, wherein digesting the biological samples comprises mixing the biological samples with a proteolytic enzyme.

3. The method of claim 2, wherein the proteolytic enzyme is selected from the group consisting of trypsin, chymotrypsin, IDeS, Proteinase K, PNGaseF, and combination thereof.

4. The method of claim 1, wherein digesting the biological samples comprises a pretreatment step prior to mixing the biological samples with an enzyme.

5. The method of claim 4, wherein the pretreatment step is selected from the group consisting of denaturation, reduction, alkylation, and combinations thereof.

6. The method of claim 1, wherein pooling two or more biological samples comprises pooling two to fifty biological samples.

7. The method of claim 1, wherein pooling two or more biological samples comprises pooling up to 1000 different biological samples.

8. The method of claim 1, wherein mass spectrometry comprises liquid chromatography-mass spectrometry.

9. The method of claim 1, further comprising adding a stable labeled peptide or other subunit prior to enriching the pooled two or more biological samples.

10. The method of claim 1, wherein the clinical diagnosis is for an infectious disease.

11. The method of claim 10, wherein the infectious disease is SARS-COV-2.

12. The method of claim 1, wherein solid phase extraction or solvent/salt mediated protein precipitation is applied prior to enriching the pooled two or more biological samples.

* * * * *